US006994889B2

(12) United States Patent
Satomi et al.

(10) Patent No.: US 6,994,889 B2
(45) Date of Patent: Feb. 7, 2006

(54) HARD COATING PREPARATION, COATING LIQUID AND MANUFACTURING PROCESS OF HARD COATING PREPARATION

(75) Inventors: Megumi Satomi, Shizuoka (JP); Shinya Oda, Shizuoka (JP); Shiho Sogawa, Shizuoka (JP); Tsuyoshi Ito, Shizuoka (JP)

(73) Assignee: Towa Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 10/475,986

(22) PCT Filed: Jan. 31, 2003

(86) PCT No.: PCT/JP03/01025

§ 371 (c)(1),
(2), (4) Date: Oct. 27, 2003

(87) PCT Pub. No.: WO03/063603

PCT Pub. Date: Aug. 7, 2003

(65) Prior Publication Data

US 2004/0156993 A1    Aug. 12, 2004

(30) Foreign Application Priority Data

Jan. 31, 2002  (JP) ............................. 2002-024372
Jan. 30, 2003  (JP) ............................. 2003-022846

(51) Int. Cl.
B05D 3/00         (2006.01)

(52) U.S. Cl. .................................................. 427/384

(58) Field of Classification Search ................. 427/384
See application file for complete search history.

(56) References Cited

U.S. PATENT DOCUMENTS 3,527,646 A * 9/1970 Jokay et al. ................. 426/289

FOREIGN PATENT DOCUMENTS

| EP | 273000 A1 | | 6/1988 |
| EP | 273856 | * | 7/1988 |
| JP | 61-263915 A1 | | 11/1986 |
| JP | 02-207745 A1 | | 8/1990 |
| JP | 06-70688 A1 | | 3/1994 |
| JP | 06-292511 A1 | | 10/1994 |
| JP | 11-127785 A1 | | 5/1999 |
| JP | 2000-316479 A1 | | 11/2000 |
| JP | 2001-069915 | * | 3/2001 |
| JP | 2002-17266 A1 | | 1/2002 |
| WO | WO-00/18835 A1 | | 4/2000 |
| WO | WO 01/92401 | * | 12/2001 |
| WO | WO 2003/000068 | * | 1/2003 |

OTHER PUBLICATIONS

Lawson et al, Royan Society of Chemistry, 218 (Gums and Stabilizers for the Food Industry 9), pp 76-83, 1998.*
Abstract of Bogusz, Manufacturing Confectioner, 84(8), pp 39-46, Aug. 2004.*

* cited by examiner

Primary Examiner—Erma Cameron
(74) Attorney, Agent, or Firm—Rader, Fishman & Grauer PLLC

(57) ABSTRACT

The present invention provides hard coating preparation having a hard coating layer, unbreakable, made from sugar/sugar alcohols and oxidized starch and/or acid treated starch, with low waste of coating liquid when forming the coating layer.

The hard coating preparation has the hard coating layer containing any one of sugar/sugar alcohols selected from the group of maltitol, xylitol, erythritol, mannitol, lactitol, PALATINIT (registered trade mark), trehalose, sucrose, and oxidized starch and/or acid treated starch.

10 Claims, 1 Drawing Sheet

HARD COATING PREPARATION, COATING LIQUID AND MANUFACTURING PROCESS OF HARD COATING PREPARATION

TECHNICAL FIELD

The present invention relates to hard coating preparation and coating liquid as raw material for making hard coating layer and to a manufacturing process of hard coating preparation.

BACKGROUND ART

Hard coating preparation having hard coating layer made from sugar/sugar alcohol is defective not only in poor shock resistance such as shown by cracks on the surface of easily broken coating layer due to poor adhesion of sugar/sugar alcohol crystals respectively forming a coating layer, lack of flexibility in obtained coating layer, softness of the coating layer, etc. but also in high percentage of wasted coating liquid due to poorly adhering to the coating center while adhering more to the coating pan during production.

Such problems are marked in accordance with the increase of sugar/sugar alcohol content in coating layer.

Various additives are proposed to be used in the art to cover such defects of a coating layer made from sugar/sugar alcohols.

For example, water soluble macromolecular substances such as pullulan, gelatin, gum arabic are used as coating reinforcing agents in producing hard coating preparations having a coating layer with maltitol (see Japanese Patent Publication No. 7-55898).

However, the above substances used as coating reinforcing agents are newly defective, as they are difficult to handle due to high increase in viscosity when put in water solution, coating layer is browned with lapse of time, it takes long time for formation of coating layer, etc.

Moreover, those coating reinforcing agents are very expensive, as another disadvantage.

Then, use of xylitol for coating has been disclosed (see Japanese Patent Publication No. 5-14535).

However, it requires a plurality of additives such as film forming agent, binder, and filler as ingredients other than xylitol. In addition, coating liquid does not spread well when sprayed on the surface of coating center due to high viscosity of coating liquid, cracking the surface of the coating layer and failing to finish a pretty appearance of the product.

In other words, the object of the present invention is to provide a hard coating preparation having a hard coating layer, unbreakable, made from specific sugar/sugar alcohols, with low waste of coating liquid when forming the coating layer.

DISCLOSURE OF THE INVENTION

The present inventors found out that a hard coating layer made from any one of sugar/sugar alcohols such as maltitol, xylitol, erythritol, mannitol, lactitol, PALATINIT (registered trade mark which trade mark is hereinafter understood to mean "mixture of α-D-giucopyranosyl-1,6-sorbitol and α-D-glucopyranosyl-1,1-mannitol), trehalose, sucrose, can be effectively unbreakable by adding oxidized starch and/or acid treated starch to the sugar/sugar alcohols, also reducing waste of coating liquid when forming the coating layer, while keeping it equal to or better than the conventional ones in smoothness and crunchiness of the coating layer felt when crunched in mouth.

In other words, problems are solved in the present invention by the following means.

The first means is hard coating preparation having a hard coating layer containing any one sugar/sugar alcohol selected from the group of maltitol, xylitol, erythritol, mannitol, lactitol, PALATINIT (registered trade mark), trehalose, sucrose as well as oxidized starch and/or acid treated starch.

The second means is hard coating preparation according to the above first means in which the coating layer contains, as solid content, 35.00 to 99.99% sugar/sugar alcohol and 0.01 to 65.00% oxidized starch and/or acid treated starch by weight as calculated on a solid basis.

The third means is hard coating preparation according to the above first or second means further containing, in addition to sugar/sugar alcohol and oxidized starch and/or acid treated starch, coating reinforcing agent and/or suspension base.

The fourth means is hard coating preparation according to any one of the above first to third means in which the sugar/sugar alcohol is maltitol.

The fifth means is coating liquid containing, in the form of dissolved solid ingredients, 80.00 to 99.99% any one sugar/sugar alcohol selected from the group of maltitol, xylitol, erythritol, mannitol, lactitol, PALATINIT (registered trade mark), trehalose, sucrose by weight as well as 0.01 to 20.00% oxidized starch and/or acid treated starch by weight, calculated on a solid basis.

The sixth means is coating liquid according to the above fifth means characterized by containing coating reinforcing agent and/or suspension base.

The seventh means is coating liquid according to the above fifth or sixth means in which the sugar/sugar alcohol is maltitol.

The eighth means is manufacturing process of hard coating preparation characterized by alternately repeating a liquid pouring step where coating liquid according to any one of the above fifth to seventh means is poured on a coating center and a drying step where the coating center wet with the liquid is dried.

The term "coating center" here refers to what is simply called center, center tablet, core, naked tablet, core tablet, etc.

The ninth means is manufacturing process of hard coating preparation according to the above eighth means having a powder dusting step to dust over the coating center mixture powder of any one or two or more selected from the group of maltitol, xylitol, erythritol, mannitol, lactitol, PALATINIT (registered trade mark), trehalose, sucrose, oxidized starch, acid treated starch, coating reinforcing agent, suspension base.

The tenth means is manufacturing process of hard coating preparation according to the above eighth or ninth means characterized by use of coating liquid in which the coating liquid according to any one of the above fifth to seventh means is further mixed and suspended with powder consisting of any one or two or more of solid ingredients contained in coating liquid.

The term "hard coating preparation" in the present invention refers to the preparation which a coating center is coated with a hard coating layer containing particular sugar/sugar alcohol as well as oxidized starch and/or acid treated starch.

Hard coating preparation obtained from such combination is characterized by its excellently smooth coating surface, unbreakable coating layer, crunchiness when crunched in mouth, etc.

Hard coating preparation of the present invention should contain in its coating layer particular sugar/sugar alcohol as well as oxidized starch and/or acid treated starch.

Usually, the coating layer should contain, in the form of solid ingredients, calculated on a solid basis, 35.00 to 99.99% sugar/sugar alcohol, 0.01 to 65.00% oxidized starch and/or acid treated starch by weight, preferably 50.00 to 99.90% sugar/sugar alcohol, 0.10 to 50.00% oxidized starch and/or acid treated starch by weight, more preferably 70.00 to 99.00% sugar/sugar alcohol, 1.00 to 30.00% oxidized starch and/or acid treated starch by weight, and preferably in particular 90.00 to 98.00% sugar/sugar alcohol, 2.00 to 10.00% oxidized starch and/or acid treated starch by weight.

Hard coating preparation of the present invention is characterized by its unbreakable coating layer as assessed by a test in which the hard coating preparation is subjected to a free fall from 30 cm high above smooth marble to count how many times it must fall to break the coating layer on the surface. According to the test results, it has proved to be less breakable than the conventional coating preparation having no content of oxidized starch and/or acid treated starch, whichever sugar/sugar alcohol may be used to make the hard coating preparation.

Hard coating preparation of the present invention is better in smoothness of the coating layer surface than coating preparation with conventional coating reinforcing agent or made only from sugar/sugar alcohol, thereby allowing the coating preparation to look better in appearance.

Any sugar/sugar alcohol, good enough in quality to be marketed for food or medicine, can be used in the present invention, regardless of origin, manufacturing process or shape.

The present invention uses for the hard coating preparation sugar/sugar alcohol selected from the group of maltitol, xylitol, erythritol, mannitol, lactitol, trehalose, PALATINIT (registered trade mark) and sucrose. Preferred among them for crunchy and refreshingly cool taste when crunched in mouth are maltitol, xylitol, erythritol, PALATINIT (registered trade mark), lactitol respectively and maltitol is more preferred for excellent smoothness, strength and crunchiness of coating layer. Moreover, crystalline maltitol or crystalline mixture solid containing maltitol is particularly preferred and crystalline maltitol is preferred the best.

PALATINIT (registered trade mark) means mixture of α-D-glucopyranosyl-1,6-sorbitol (here after sometimes abbreviated as GPS) and α-D-glucopyranosyl-1,1-mannitol (here after sometimes abbreviated as GPM). Marketed products such as PALATINIT and coating PALATINiT (both registered trade marks produced by Shin Mitsui Sugar Co., Ltd.) can be advantageously used.

Sugar/sugar alcohol used in the present invention can be used in any form of crystal, crystalline mixture solid and liquid. However, except for PALATINIT (registered trade mark), high purity products containing 90.00% or more, preferably 95.00% or more, more preferably 98.00% or more sugar/sugar alcohol by weight calculated on a solid basis can advantageously be used in view of time needed for formation of coating layer, unbreakableness and smoothness of coating layer.

Oxidized starch used in the present invention means starch derivatives produced by adding oxidant such as sodium hypochlorite, periodic acid, etc. to starch suspended liquid, followed by refining and drying the liquid. Then, acid treated starch means starch derivatives produced by adding acids such as hydrochloric acid, sulfuric acid, etc. to starch suspended liquid, agitating it for a predetermined period of time, followed by refining and drying the liquid. Such oxidized starch or acid treated starch can be used, if marketed as food or medicine or prepared by the publicly known method.

There is no particular restriction about types of starch as raw materials for oxidized starch and/or acid treated starch used in the present invention. In other words, cereal starch such as corn starch, waxy corn starch, high amylose corn starch, wheat starch, rice starch, sago starch, root and tuber starch such as potato starch, sweet potato starch, tapioca starch, etc. can be used but waxy corn starch, potato starch, tapioca starch are preferred in particular, thanks to their slow retrogradation and easiness to handle in production of coating.

Oxidized starch and/or acid treated starch can be used in the present invention, as subjected to esterification such acetylation, phosphorylation, succination, etc. or etherealization such as hydroxypropylation, hydroxyethylation, etc. Then, esterification is preferred for easy preparation and low costs and acetylation is more preferable.

Oxidized starch and/or acid treated starch used in the present invention is put in suspended liquid with water added to be heated at 95° C. for ten minutes till complete dissolution of oxidized starch and/or acid treated starch, then cooled down to 50° C. to obtain a water solution with solid content of 25.00% by weight. Thus obtained water solution should have a viscosity of 10 to 1000 cP or preferably 50 to 500 cP as measured by a B type viscometer to make it easy to handle as a coating liquid.

Suspension bases and/or coating reinforcing agents may be contained in hard coating preparation of the present invention for the purpose of improving coating layer in hardness, whiteness, crunchiness, shock resistance, etc. also preventing the coating center from hygroscopicity.

Mixture of one or two or more selected from talc, kaolin, calcium carbonate, calcium sulfate, calcium hydrogenphosphate, titanium dioxide, silicon dioxide, magnesium siliconaluminate, calcium silicate, magnesium silicate, aluminum magnesium silicate, silicic anhydride, crystalline cellulose, eggshell calcium, seashell calcium, bone meal, aluminum stearate, calcium stearate, magnesium stearate, can be used as a suspension base in the present invention and all of them are non-soluble or hardly soluble in water unlike other water-soluble ingredients.

Addition of such suspension bases mainly allows improvement in whiteness of the coating layer and in prevention from hygroscopicity against the coating center in the hard coating preparation by the coating layer.

Various types of water soluble macromolecular substances used in formation of coating layer can be used as coating reinforcing agents for hard coating preparation of the present invention. For example, it should preferably be mixture of one or two or more selected from gum arabic, pullulan, gelatin, dextrin, hydroxymethyl cellulose, carboxymethyl cellulose, polyvinyl pyrrolidone, polyvinyl alcohol, hydroxypropyl methyl cellulose. Then, dextrin can be not only usual one but also products marketed as branched dextrin or its hydride can also advantageously be used.

Coating liquid according to the present invention contains ingredients to coat the surface of coating center as an object to be coated and to form the coating layer.

Coating liquid prepared to realize the present invention should preferably contain, in the form of water soluble solid ingredients dissolved in the coating liquid, 80.00 to 99.99% sugar/sugar alcohol and 0.01 to 20.00% oxidized starch and/or acid treated starch by weight as calculated on a solid ingredients basis. Otherwise, it may take longer to form a coating layer or roughness may be more likely to occur on the coating layer, as affected by sugar/sugar alcohol content lower than 80.00% by weight. Then, the advantageous effects of the present invention can not be sufficiently obtained, when it contains only less than 0.01% oxidized starch and/or acid treated starch by weight.

To prepare coating liquid according to the present invention, it starts with addition of oxidized starch and/or acid treated starch to cold or hot water, which is heated as needed till complete dissolution of the oxidized starch and/or acid treated starch, followed by addition and dissolution of sugar/sugar alcohol and finally diluted or concentration to get a predetermined concentration of thus obtained water solution.

Otherwise, it may start with addition of oxidized starch and/or acid treated starch to cold or hot water which is heated as needed till complete dissolution of the oxidized starch and/or acid treated starch to obtain a water solution. Then, the water solution is mixed with another water solution containing dissolved sugar/sugar alcohol. Thus obtained water solution is diluted or concentrated to a predetermined concentration to prepare a coating liquid.

The second method may be adopted to make it easy to prepare a coating liquid containing completely dissolved oxidized starch and/or acid treated starch.

Suspension bases and/or coating reinforcing agents may be added to the coating liquid of the present invention, in addition to water soluble ingredients consisting of sugar/sugar alcohol and oxidized starch and/or acid treated starch.

Mixture of one or two or more selected from talc, kaolin, calcium carbonate, calcium sulfate, calcium hydrogenphosphate, titanium dioxide, silicon dioxide, magnesium siliconaluminate, calcium silicate, magnesium silicate, magnesium silicate, aluminum magnesium silicate, silicic anhydride, crystalline cellulose, eggshell calcium, seashell calcium, bone meal, aluminum stearate, calcium stearate, magnesium stearate, can be used as a suspension base in the present invention and all of them are non-soluble or hardly soluble in water ingredients, which are distinguished from other water-soluble ones.

Suspension base containing coating liquid is prepared by addition of such suspension bases into the coating liquid, which mainly allows improvement in whiteness of the coating layer and in prevention of the coating layer from; hygroscopicity.

Various types of water soluble macromolecular substances can be added into the coating liquid of the present invention, as coating reinforcing agents, in addition to water soluble ingredients consisting of sugar/sugar alcohol and oxidized starch and/or acid treated starch.

As for coating reinforcing agents according to the present invention, various types of water soluble macromolecular substances are used in forming a coating layer. For example, it should preferably be mixture of one or two or more selected from gum arabic, pullulan, gelatin, dextrin, hydroxymethyl cellulose, carboxymethyl cellulose, polyvinyl pyrrolidone, polyvinyl alcohol, hydroxypropyl methyl cellulose. Then, dextrin can be not only usual one but also products marketed as branched dextrin or its hydride can also advantageously be used.

Coating liquid according to the present invention can be used as suspended, with powder mixture mixing any one or two or more of sugar/sugar alcohol, oxidized starch, acid treated starch, suspension bases, coating reinforcing agents, such as dissolved in coating liquid, further added to the coating liquid.

Coating liquid according to the present invention is excellent in adhesion to the coating center and allows reduction of coating liquid wasted e.g. as adhered to a coating pan during production of hard coating preparation.

Hard coating preparation according to the present invention can be advantageously produced by a continuously or discontinuously rotating device such as a coating pan charged with a coating center, alternately repeating a liquid pouring step to spray the above described coating liquid over the coating center rotating inside the rotation device, and then a drying step to dry the coating center wet with the liquid to precipitate and solidify on the coating center the solid ingredients of the coating liquid, till formation of a coating layer as thick as desired. However, other publicly known methods used to form a coating layer can be adopted to make hard coating preparation covered with hardened coating layer around the coating center.

To produce hard coating preparation according to the present invention, a powder dusting step to dust powdered material directly over the coating center may be introduced and realized, as needed, at any stage to form a hard coating layer, in addition to the liquid pouring and drying steps.

Powdered material used at the powder dusting step should preferably be ingredients usually contained in a coating liquid or mixture of one or two or more selected from the group of maltitol, xylitol, erythritol, mannitol, lactitol, PALATINIT (registered trade mark), trehalose, sucrose, oxidized starch, acid treated starch, suspension bases, coating reinforcing agents. Then, sugar/sugar alcohols should preferably be used in the form of crystal or crystalline mixture solid.

There is no particular restriction about when to carry out the powder dusting step but it should preferably be done immediately after completion of the coating liquid pouring step or after the coating liquid has been uniformly distributed all over the coating center, in order to spread uniformly the powdered material over the coating center, to dry the coating liquid sprayed over the coating center and to form the coating layer more quickly, etc.

There is no particular restriction about how many times to dust powder to form the hard coating layer of the present invention. Powder may be dusted for a plurality of cycles, in the order of liquid pouring, powder dusting and drying steps, or may be intermittently dusted at any stage till formation of a hard coating layer as thick as desired.

Hard coating preparation of the present invention can advantageously be prepared by a method consisting in adding an excessive amount of powdered product such as sugar/sugar alcohol, oxidized starch, acid treated starch, suspension base, coating reinforcing agent, etc. into usually used coating liquid to make a suspended coating liquid to be poured on a coating center, followed by alternate repetition of liquid pouring and drying steps, or by another method e.g. consisting in inserting a powder dusting step at any stage.

In preparing hard coating preparation of the present invention, dry air should preferably be continuously or discontinuously ventilated to dry quickly the coating liquid sprayed and adhered on the coating center. However, there is no particular restriction about conditions in ventilating the air, as long as the present invention is advantageously realized.

In preparing hard coating preparation of the present invention, crystallization, precipitation and solidification of solid ingredients contained in the coating liquid can be facilitated or water contained in the coating liquid may be inhibited from moving to the coating center by carrying out, after spraying the coating liquid over the coating center, a powder dusting step consisting in spreading powder of mixture mixing one or two or more selected from powdered crystals or crystalline mixture solid of sugar/sugar alcohol ingredients such as maltitol, xylitol, erythritol, mannitol, lactitol, PALATINIT (registered trade mark), trehalose, sucrose, etc., oxidized starch, acid treated starch, coating reinforcing agent, suspension base, which is contained in the coating liquid.

In preparing hard coating preparation of the present invention, powdered materials used at a powder dusting step or to make a suspended coating liquid should preferably be of the same ingredients as sugar/sugar alcohol, oxidized starch, acid treated starch, coating reinforcing agent, suspension base contained in the coating liquid and the sugar/sugar alcohol should preferably be crystals or crystalline mixture solid.

To dust powder on the coating center, after spraying a coating liquid over it, the coating center should preferably be continuously or discontinuously rotating or moving, in order to prevent powder from coagulation or lumping, for easier uniform distribution all over the coating center, etc.

In the practice of the present inventions, there is no particular restriction about material to make a coating center, allowing use of tablet, gum, candy, gumi candy, soft capsule, etc.

There is no particular restriction in shaping the coating center, allowing it to be shaped in any form of sphere, pillow, bale, triangle, quadrangle, cube, etc.

The present invention can be realized without any problem, mixing e.g. various sour condiments such as citric acid, malic acid, vitamins such as vitamins B2, C, various amino acids such as glycin, alanine, highly sweet sweetening such as aspartame, stevioside, saccharin, rebaudioside A, trichlorosucrose, various galenical such as mint, herb, menthol, fruit flavors such as apple, strawberry, melon, orange, various relish flavors such as coffee flavor, cocoa flavor, etc., for better taste, or adding synthetic or natural colorant. Then, there is no particular restriction about how to add such additives, as they should only be contained in hard coating preparation in the end. For example, such ingredients may be dissolved beforehand in the coating liquid or such additives may be sprayed directly during formation of a coating layer.

ADVANTAGEOUS EFFECTS OF THE INVENTION

Figure 1:
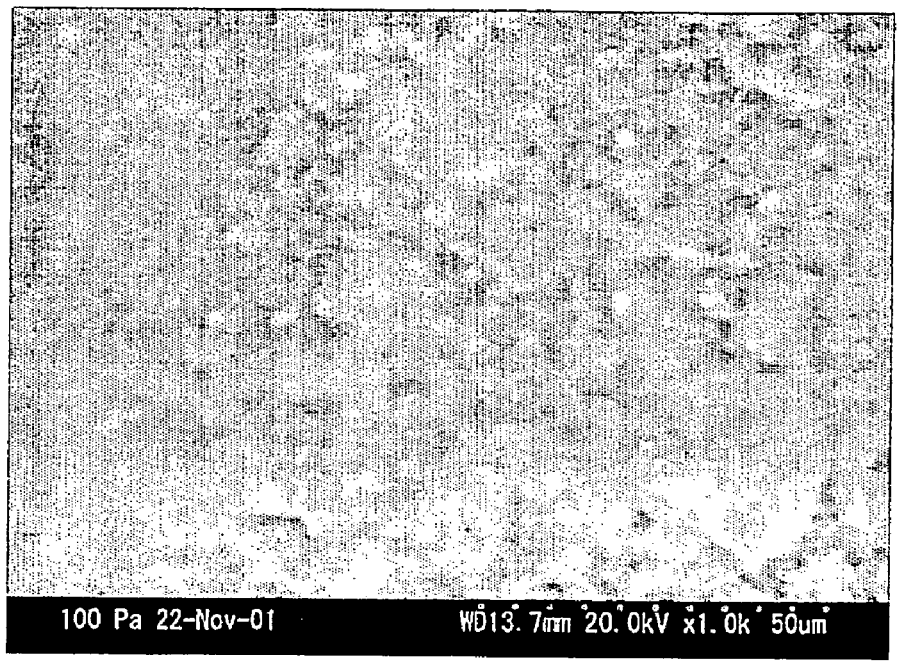
FIG. 1 is an electronic microscopic picture of the coating layer surface of inventive product 1 with magnification of ×1000.

The present invention provides hard coating preparation with unbreakable coating layers made from sugar/sugar alcohol and oxidized starch and/or acid treated starch, reducing waste of coating liquid in forming the coating layer.

Moreover, the present invention allows to abridge a time to form the coating layer and to provide hard coating preparation equal to or better than the conventional ones in smoothness and crunchiness of the coating layer.

BEST MODE OF REALIZATIOAN OF THE INVENTION

EXAMPLES

The present invention will be more specifically explained here after, referring to examples of realization and preparation, which do not restrict the technical scope of the present invention. Unless otherwise mentioned, % in the following Examples means % by weight.

Then, comparative tests will be explained, followed by Tables 1 and 2 showing compositions of coating liquids in the respective Examples.

In addition, compositions of coating liquids in the respective comparative examples will be shown in FIG. 3 after explanation of comparative tests.

Preparation Example 1

Preparation of Oxidized Tapioca Starch

1 Kg of tapioca starch (produced by Nihon Shokuhin Kako Co., Ltd.) was added to 2 Kg of water to make a suspended liquid and it was heated up to 30° C. Then, water solution of 3% sodium hydroxide was added to the suspended liquid to adjust pH to be 11.0 and it was subjected to oxidation treatment for one hour with addition of 150 ml of sodium hypochlorite solution containing 13% effective chlorine, followed by neutralization with hydrochloric acid to be washed with water, dewatered and dried to prepare oxidized tapioca starch.

Preparation Example 2

Preparation of Oxidized Corn Starch

Oxidized corn starch was prepared by the same method as in Preparation Example 1 except for corn starch (produced by Nihon Shokuhin Kako Co., Ltd.) as raw material in place of tapioca starch.

Preparation Example 3

Preparation of Oxidized Acetylated Tapioca Starch

1 Kg of tapioca starch (produced by Nihon Shokuhin Kako Co., Ltd.) was added to 2 Kg of water to make a suspended liquid and it was heated up to 30° C. Then, water solution of 3% sodium hydroxide was added to the suspended liquid to adjust pH to be 11.0 and it was subjected to oxidation treatment for one hour with addition of 150 ml of sodium hypochlorite solution containing 13% effective chlorine, followed by adjusting pH to be 10.0 with hydrochloric acid and it was subjected to acetylating reaction for one hour with addition of 50 ml of vinyl acetate (monomer). It was neutralized with hydrochloric acid to be washed with water, dewatered and dried to prepare oxidized acetylated tapioca starch.

Preparation Example 4

Preparation of Acid Treated Tapioca Starch

1 Kg of tapioca starch (produced by Nihon Shokuhin Kako Co., Ltd.) was added to 2 Kg of water to make suspension with addition of 40 ml of hydrochloric acid and was acid treated as agitated at 40° C. for 5 hours. Then, it was neutralized with 3% sodium hydroxide solution to be washed with water, dewatered and dried to prepare acid treated tapioca starch.

Preparation Example 5

Preparation of Oxidized Potato Starch

Oxidized potato starch was prepared by the same method as in Preparation Example 1 except for potato starch (primary reagent, produced by Kanto Kagaku) as raw material in place of tapioca starch.

Preparation Example 6

Preparation of Oxidized Waxy Corn Starch

Oxidized waxy corn starch was prepared by the same method as in Preparation Example 1 except for waxy corn starch (waxy starch produced by Nihon Shokuhin Kako Co., Ltd.) as raw material in place of tapioca starch.

Preparation Example 7

Preparation of Coating Center

Tablet prepared by the following process was used as a coating center to be coated with a coating layer.

Tablet was made from 70 parts by weight of maltitol (named "Powder Maltitol G-3" produced by Towa Chemical Industry Co., Ltd.), 30 parts by weight of vitamin C (produced by Towa Chemical Industry Co., Ltd.) and 2 parts by weight of sucrose fatty acid ester (named "DKS F-20W" produced by Dai-Ichi Kogyo Seiyaku Co., Ltd.), fully mixed as marketed respectively.

Raw material for tablet as prepared at the above blending ratio was directly compressed by a rotary tableting machine (named "8F-3" produced by Kikusui Seisakusho Ltd.) having an upper pounder calibrated at 1 mm and a lower pounder calibrated at 5 mm and a pounder of 10 mm×8.5 R to obtain tablets having a diameter of 10 mm, thickness of 4.7 mm and a weight of 320 mg/tablet at an average, which were used as coating centers.

Example 1

Maltitol/Oxidized Acetylated Tapioca Starch

Coating liquid was made from maltitol (named "LESYS" registered trade mark produced by Towa Chemical Industry Co., Ltd.) and oxidized acetylated tapioca starch prepared by preparation example 3.

To prepare coating liquid, oxidized acetylated tapioca starch was added to water, heated till boiling and was kept as boiling till complete dissolution of oxidized acetylated tapioca starch in water.

Maltitol was added, after complete dissolution of oxidized acetylated tapioca starch, and was completely dissolved to prepare coating liquid containing 65.00% maltitol, 3.00% oxidized acetylated tapioca starch and 32.00% water by weight.

1000 tablets of coating centers prepared in preparation example 7 were put into a small coating machine (named "16DS" produced by Kikusui Seisakusho Ltd.). Then, 4 g of coating liquid at a temperature of 60° C. was sprayed at one time on coating centers inside the continuously rotating small coating machine, discontinuously ventilating with air streams on the coating centers inside the small coating machine to dry the surface of the coating centers. This routine was repeated to perform the coating to obtain hard coating preparation (inventive product 1) having a weight of 540 mg/tablet at an average.

Inventive product 1 contained in its coating layer 95.59% maltitol and 4.41% oxidized acetylated tapioca starch by weight as solid ingredients.

Example 2

Maltitol/Oxidized Tapioca Starch

Coating liquid containing 65.00% maltitol, 3.00% oxidized tapioca starch, 32.00% water by weight was prepared by the same method as in Example 1 except for use of oxidized tapioca starch prepared in preparation example 1 in place of oxidized acetylated tapioca starch in Example 1.

Coating was performed in the same way as in Example 1 with thus prepared coating liquid to obtain hard coating preparation (inventive product 2) having a weight of 540 mg/tablet at an average.

Inventive product 2 contained in its coating layer 95.59% maltitol and 4.41% oxidized tapioca starch by weight as solid ingredients.

Example 3

Maltitol/Oxidized Corn Starch

Coating liquid containing 65.00% maltitol, 3.00% oxidized corn starch, 32.00% water by weight was prepared by the same method as in Example 1 except for use of oxidized corn starch prepared in preparation example 2 in place of oxidized acetylated tapioca starch in Example 1.

Coating was performed in the same way as in Example 1 with thus prepared coating liquid to obtain hard coating preparation (inventive product 3) having a weight of 540 mg/tablet at an average.

Inventive product 3 contained in its coating layer 95.59% maltitol and 4.41% oxidized corn starch by weight as solid ingredients.

Example 4

Maltitol/Oxidized Acetylated Tapioca Starch/Suspension Base

Suspended coating liquid containing 51.00% maltitol, 3.00% oxidized acetylated tapioca starch, 7.00% calcium carbonate, 7.00% talc and 32.00% water by weight was prepared by the same method as in Example 1 except for use of calcium carbonate (primary reagent produced by Kanto Kagaku) and talc (primary reagent produced by Kanto Kagaku) as suspension bases in addition to maltitol (named "LESYS" produced by Towa Chemical Industry Co., Ltd.) and oxidized acetylated tapioca starch prepared in preparation example 3 as raw materials for coating liquid.

Coating was performed in the same way as in Example 1 with thus prepared suspended coating liquid to obtain hard coating preparation (inventive product 4) having a weight of 540 mg/tablet at an average.

Inventive product 4 contained in its coating layer 75.00% maltitol, 4.41% oxidized acetylated tapioca starch, 10.29% calcium carbonate, 10.29% talc (20.59% suspension base of calcium carbonate+talc) by weight as solid ingredients.

Example 5

Maltitol/Oxidized Potato Starch

Coating liquid containing 65.00% maltitol, 3.00% oxidized potato starch, 32.00% water by weight was prepared by the same method as in Example 1 except for use of oxidized potato starch prepared in preparation example 5 in place of oxidized acetylated tapioca starch used in Example 1.

Coating was performed in the same way as in Example 1 with thus prepared coating liquid to obtain hard coating preparation (inventive product 5) having a weight of 540 mg/tablet at an average.

Inventive product 5 contained in its coating layer 95.59% maltitol and 4.41% oxidized potato starch by weight as solid ingredients.

Example 6

Maltitol/Oxidized Waxy Corn Starch

Coating liquid containing 65.00% maltitol, 3.00% oxidized waxy corn starch, 32.00% water by weight was prepared by the same method as in Example 1 except for use of oxidized waxy corn starch prepared in preparation example 6 in place of oxidized acetylated tapioca starch used in Example 1.

Coating was performed in the same way as in Example 1 with thus prepared coating liquid to obtain hard coating preparation (inventive product 6) having a weight of 540 mg/tablet at an average.

Inventive product 6 contained in its coating layer 95.59% maltitol and 4.41% oxidized waxy corn starch by weight as solid ingredients.

Example 7

Maltitol/Oxidized Tapioca Starch/Oxidized Potato Starch

Coating liquid containing 65.00% maltitol, 0.90% oxidized tapioca starch, 2.10% oxidized potato starch, 32.00% water by weight was prepared by the same method as in Example 1 except for use of oxidized tapioca starch prepared in preparation example 1 and oxidized potato starch prepared in preparation example 5 in place of oxidized acetylated tapioca starch used in Example 1.

Coating was performed in the same way as in Example 1 with thus prepared coating liquid to obtain hard coating preparation (inventive product 7) having a weight of 540 mg/tablet at an average.

Inventive product 7 contained in its coating layer 95.59% maltitol, 1.32% oxidized tapioca starch and 3.09% oxidized potato starch by weight as solid ingredients.

Example 8

Maltitol/Oxidized Tapioca Starch with Maltitol Powder Dusted

Coating liquid containing 65.00% maltitol, 3.00% oxidized tapioca starch, 32.00% water by weight was prepared by the same method as in Example 1 except for use of oxidized tapioca starch prepared in preparation example 1 in place of oxidized acetylated tapioca starch used in Example 1.

Then, crystalline maltitol powder (named "LESYS fine powder" produced by Towa Chemical Industry Co., Ltd.) was used at a powder dusting step.

Next, 1000 tablets of coating centers produced in preparation example 7 were put into a small coating machine and 4 g of prepared coating liquid at a temperature of 60° C. was sprayed at one time over the coating centers inside the continuously rotating small coating machine.

After uniform adhesion of coating liquid over the coating centers, 4 g of crystalline maltitol powder was uniformly spread all over the coating centers by powder dusting operation.

Then, the coating centers in the small coating machine were discontinuously ventilated with air streams to dry the surface of coating centers.

A step, thus starting from spraying coating liquid over the coating centers and finishing with drying the coating centers, was repeated till the coating centers have a weight of 384 mg/tablet at an average to form a coating layer.

No powder was dusted after the coating centers got a weight of 384 mg/tablet at an average but coating was performed instead, repeating spraying coating liquid and drying in the same way as in Example 1, till getting a weight of 540 mg/tablet at an average to obtain hard coating preparation (inventive product 8).

Inventive product 8 contained in its coating layer 96.35% maltitol and 3.65% oxidized tapioca starch by weight as solid ingredients.

Example 9

Maltitol/Oxidized Tapioca Starch with Maltitol Powder and Oxidized Tapioca Starch Powder Dusted Coating liquid containing 65.00% maltitol, 3.00% oxidized tapioca starch, 32.00% water by weight was prepared by the same method as in Example 1 except for use of oxidized tapioca starch prepared in preparation example 1 in place of oxidized acetylated tapioca starch used in Example 1.

Then, powder mixture containing 70.00% crystalline maltitol powder (named "LESYS fine powder" produced by Towa Chemical Industry Co., Ltd.), 30.00% oxidized tapioca starch prepared in preparation example 1 by weight, prepared by fully mixing the ingredients, was used at a powder dusting step.

As in Example 8, 1000 tablets of coating centers produced in preparation example 7 were put into a small coating machine and 4 g of prepared coating liquid at a temperature of 60° C. was sprayed at one time over the coating centers inside the continuously rotating small coating machine.

After uniform adhesion of coating liquid over the coating centers, 4 g of powder mixture of crystalline maltitol powder and oxidized tapioca starch was uniformly spread all over the coating centers by powder dusting operation.

Then, the coating centers in the small coating machine were discontinuously ventilated with air streams to dry the surface of coating centers.

A step, thus starting from spraying coating liquid over the coating centers and finishing with drying the coating centers, was repeated till the coating centers got a weight of 384 mg/tablet at an average to form a coating layer.

No powder was dusted after the coating centers got a weight of 384 mg/tablet at an average but coating was performed instead, repeating spraying coating liquid and drying in the same way as in Example 1, till getting a weight of 540 mg/tablet at an average to obtain hard coating preparation (inventive product 9).

Inventive product 9 contained in its coating layer 91.16% maltitol and 8.84% oxidized tapioca starch by weight as solid ingredients.

Example 10

Maltitol/Oxidized Tapioca Starch with Maltitol, Oxidized Tapioca Starch and Suspension Base Powder Dusted Coating liquid containing 65.00% maltitol, 3.00% oxidized tapioca starch, 32.00% water by weight was prepared by the same method as in Example 1 except for use of oxidized tapioca starch prepared in preparation example 1 in place of oxidized acetylated tapioca starch used in Example 1.

Then, powder mixture containing 20.00% crystalline maltitol powder (named "LESYS fine powder" produced by Towa Chemical Industry Co., Ltd.), 70.00% oxidized tapioca starch prepared in preparation example 1 and 10.00% calcium carbonate (primary reagent produced by Kanto Kagaku) by weight, prepared by fully mixing the ingredients, was used at a powder dusting step.

As in Example 8, 1000 tablets of coating centers produced in preparation example 7 were put into a small coating machine and 4 g of prepared coating liquid at a temperature of 60° C. was sprayed at one time over the coating centers inside the continuously rotating small coating machine.

After uniform adhesion of coating liquid over the coating centers, 10 g of powder mixture of crystalline maltitol powder and oxidized tapioca starch was uniformly spread all over the coating centers by powder dusting operation.

Then, the coating centers in the small coating machine were discontinuously ventilated with air streams to dry the surface of coating centers.

A step, thus starting from spraying coating liquid-over the coating centers and finishing with drying the coating centers, was repeated till the coating centers got a weight of 480 mg/tablet at an average to form a coating layer.

No powder was dusted after the coating centers got a weight of 480 mg/tablet at an average but coating was performed instead, repeating spraying coating liquid and drying in the same way as in Example 1, till getting a weight of 540 mg/tablet at an average to obtain hard coating preparation (inventive product 10).

Inventive product 10 contained in its coating layer 52.37% maltitol, 41.91% oxidized tapioca starch and 5.72% calcium carbonate by weight as solid ingredients.

Example 11

Maltitol/Oxidized Tapioca Starch with Oxidized Tapioca Starch Powder Dusted

Coating liquid containing 65.00% maltitol, 3.00% oxidized tapioca starch, 32.00% water by weight was prepared by the same method as in Example 1 except for use of oxidized tapioca starch prepared in preparation example 1 in place of oxidized acetylated tapioca starch used in Example 1.

Then, oxidized tapioca starch prepared in preparation example 1 was used at a powder dusting step.

As in Example 8, 1000 tablets of coating centers produced in preparation example 7 were put into a small coating machine and 4 g of prepared coating liquid at a temperature of 60° C. was sprayed at one time over the coating centers inside the continuously rotating small coating machine.

After uniform adhesion of coating liquid over the coating centers, 12 g of oxidized tapioca starch was uniformly spread all over the coating centers by powder dusting operation.

Then, the coating centers in the small coating machine were discontinuously ventilated with air streams to dry the surface of coating centers.

A step, thus starting from spraying coating liquid over the coating centers and finishing with drying the coating centers, was repeated till the coating centers got a weight of 480 mg/tablet at an average to form a coating layer.

No powder was dusted after the coating centers got a weight of 480 mg/tablet at an average but coating was performed instead, repeating spraying coating liquid and drying in the same way as in Example 1, till getting a weight of 540 mg/tablet at an average to obtain hard coating preparation (inventive product 11).

Inventive product 11 contained in its coating layer 38.92% maltitol and 61.08% oxidized tapioca starch by weight as solid ingredients.

Example 12

Erythritol/Acid Treated Tapioca Starch

Coating liquid containing 52.00% erythritol, 5.00% acid treated tapioca starch and 43.00% water by weight was prepared by the same method as in Example 1 except for use of erythritol (produced by Mitsubishi-Kagaku Foods Corporation) and acid treated tapioca starch prepared in preparation example 4 as raw materials for coating liquid.

Coating was performed with prepared coating liquid in the same way as in Example 1 to obtain hard coating preparation having an average weight of 540 mg/tablet (inventive product 12).

Inventive product 12 contained in its coating layer 91.23% erythritol and 8.77% acid treated tapioca starch by weight as solid ingredients.

Example 13

PALATINIT/Oxidized Acetylated Tapioca Starch

Coating liquid containing 52.00% PALATINIT, 5.00% oxidized acetylated tapioca starch and 43.00% water by weight was prepared by the same method as in Example 1 except for use of PALATINIT (named "PALATINIT PNP" registered trade mark produced by Shin Mitsui Sugar Co., Ltd.) and oxidized acetylated tapioca starch prepared in preparation example 3 as raw materials for coating liquid.

Coating was performed with prepared coating liquid in the same way as in Example 1 to obtain hard coating preparation having an average weight of 540 mg/tablet (inventive product 13).

Inventive product 13 contained in its coating layer 91.23% PALATINIT and 8.77% oxidized acetylated tapioca starch by weight as solid ingredients.

Example 14

Trehalose/Oxidized Acetylated Tapioca Starch

Coating liquid containing 55.00% trehalose, 5.00% oxidized acetylated tapioca starch and 40.00% water by weight was prepared by the same method as in Example 1 except for use of trehalose (named "TREHA" produced by Hayashibara Shoji, Inc.) and oxidized acetylated tapioca starch prepared in preparation example 3 as raw materials for coating liquid.

Coating was performed with prepared coating liquid in the same way as in Example 1 to obtain hard coating preparation having an average weight of 540 mg/tablet (inventive product 14).

Inventive product 14 contained in its coating layer 91.67% trehalose and 8.33% oxidized acetylated tapioca starch by weight as solid ingredients.

Example 15

Xylitol/Oxidized Acetylated Tapioca Starch

Coating liquid containing 67.00% xylitol, 3.00% oxidized acetylated tapioca starch and 30.00% water by weight was prepared by the same method as in Example 1 except for use of xylitol (named "Xylit" produced by Towa Chemical Industry Co., Ltd.) and oxidized acetylated tapioca starch prepared in preparation example 3 as raw materials for coating liquid.

Coating was performed with prepared coating liquid in the same way as in Example 1 to obtain hard coating preparation having an average weight of 540 mg/tablet (inventive product 15).

Inventive product 15 contained in its coating layer 95.71% xylitol and 4.29% oxidized acetylated tapioca starch by weight as solid ingredients.

Example 16

Lactitol/Oxidized Acetylated Tapioca Starch

Coating liquid containing 65.00% lactitol, 3.00% oxidized acetylated tapioca starch and 32.00% water by weight was prepared by the same method as in Example 1 except for use of lactitol (named "milchen" produced by Towa Chemical Industry Co., Ltd.) and oxidized acetylated tapioca starch prepared in preparation example 3 as raw materials for coating liquid.

Coating was performed with prepared coating liquid in the same way as in Example 1 to obtain hard coating preparation having an average weight of 540 mg/tablet (inventive product 16).

Inventive product 16 contained in its coating layer 95.59% lactitol and 4.41% oxidized acetylated tapioca starch by weight as solid ingredients.

Example 17

Mannitol/Oxidized Acetylated Tapioca Starch/Suspension Base

Coating liquid containing 30.00% mannitol, 5.00% oxidized acetylated tapioca starch, 10.00% calcium carbonate, 10.00% talc and 45.00% water by weight was prepared by the same method as in Example 1 except for use of mannitol (named "Mannit S" produced by Towa Chemical Industry Co., Ltd.), oxidized acetylated tapioca starch prepared in preparation example 3 as raw materials for coating liquid, calcium carbonate (primary reagent produced by Kanto Kagaku) and talc (primary reagent produced by Kanto Kagaku) as suspension bases.

Coating was performed with prepared coating liquid in the same way as in Example 1 to obtain hard coating preparation having an average weight of 540 mg/tablet (inventive product 17).

Inventive product 17 contained in its coating layer 54.55% mannitol, 9.09% oxidized acetylated tapioca starch, 18.18% calcium carbonate and 18.18% talc by weight as solid ingredients.

Example 18

Sucrose/Oxidized Tapioca Starch

Coating liquid containing 65.00% sucrose, 3.00% oxidized tapioca starch and 32.00% water by weight was prepared by the same method as in Example 1 except for use of sucrose (named "Granulated sugar" produced by Dai-Nippon Meiji Sugar Co., Ltd.) and oxidized tapioca starch prepared in preparation example 1 as raw materials for coating liquid.

Coating was performed with prepared coating liquid in the same way as in Example 1 to obtain hard coating preparation having an average weight of 540 mg/tablet (inventive product 18).

Inventive product 18 contained in its coating layer 95.59% sucrose and 4.41% oxidized tapioca starch by weight as solid ingredients.

Comparative Example 1

Maltitol/Gum Arabic

Maltitol (named "LESYS" produced by Towa Chemical Industry Co., Ltd.) and gum arabic (super reagent produced by Kanto Kagaku) were used as raw materials for coating liquid.

To prepare coating liquid, gum arabic was added to water and was heated till boiling and was kept boiling till complete dissolution of gum arabic in water.

After complete dissolution of gum arabic, maltitol was added and completely dissolved to prepare coating liquid containing 65.00% maltitol, 3.00% gum arabic and 32.00% water by weight.

Coating was performed as in Example 1 with prepared coating liquid to obtain comparative product 1 having a weight of 540 mg/tablet at an average.

Comparative Example 2

Maltitol/Tapioca Starch

Coating liquid containing 65.00% maltitol, 3.00% tapioca starch and 32.00% water by weight was prepared in the same way as in comparative example 1 except for use of tapioca starch instead of gum arabic in comparative example 1.

Coating was performed as in Example 1 with prepared coating liquid but no crystallization of maltitol was found from coating liquid covering the coating center and no coating layer was formed. As a result, comparative product 2 was not obtained.

Comparative Example 3

Maltitol/Tapioca Roasted Dextrin

Coating liquid containing 65.00% maltitol, 3.00% tapioca roasted dextrin and 32.00% water by weight was prepared in the same way as in comparative example 1 except for use of tapioca roasted dextrin made from tapioca starch instead of gum arabic in comparative example 1.

Coating was performed as in Example 1 with prepared coating liquid to obtain comparative product 3 having a weight of 540 mg/tablet at an average.

Comparative Example 4

Maltitol/Pullulan

Coating liquid containing 65.00% maltitol, 3.00% pullulan and 32.00% water by weight was prepared in the same way as in comparative example 1 except for use of pullulan (produced by Hayashibara Shoji, Inc.) instead of gum arabic in comparative example 1.

Coating was performed as in Example 1 with prepared coating liquid to obtain comparative product 4 having a weight of 540 mg/tablet at an average.

Comparative Example 5

Maltitol/Suspension Base

Coating liquid containing 54.00% maltitol, 7.00% calcium carbonate, 7.00% talc and 32.00% water by weight was prepared with use of calcium carbonate (primary reagent produced by Kanto Kagaku) and talc (primary agent produced by Kanto Kagaku) as suspension bases instead of gum arabic in comparative example 1.

Coating was performed as in Example 1 with prepared coating liquid to obtain comparative product 5 having a weight of 540 mg/tablet at an average.

Comparative Example 6

Maltitol Alone

Coating liquid containing 68.00% maltitol and 32.00% water by weight was prepared with use of maltitol alone.

Coating was performed as in Example 1 with prepared coating liquid to obtain comparative product 6 having a weight of 540 mg/tablet at an average.

Comparative Example 7

Erythritol/Gum Arabic

Coating liquid containing 52.00% erythritol, 5.00% gum arabic and 43.00% water by weight was prepared in the same way as in Example 12 except for use of gum arabic instead of acid treated tapioca starch used in Example 12.

Coating was performed as in Example 1 with prepared coating liquid to obtain comparative product 7 having a weight of 540 mg/tablet at an average.

Comparative Example 8

PALATINIT Alone

Coating liquid containing 52.00% PALATINIT and 48.00% water by weight was prepared without use of oxidized acetylated tapioca starch used in Example 13 but using only PALATINIT.

Coating was performed as in Example 1 with prepared coating liquid to obtain comparative product 8 having a weight of 540 mg/tablet at an average.

Comparative Example 9

Trehalose Alone

Coating liquid containing 55.00% trehalose and 45.00% water by weight was prepared without use of oxidized acetylated tapioca starch used in Example 14 but using only trehalose.

Coating was performed as in Example 1 with prepared coating liquid to obtain comparative product 9 having a weight of 540 mg/tablet at an average.

Comparative Example 10

Xylitol Alone

Coating liquid containing 67.00% xylitol and 33.00% water by weight was prepared without use of oxidized acetylated tapioca starch used in Example 15 but using only xylitol.

Coating was performed as in Example 1 with prepared coating liquid to obtain comparative product 10 having a weight of 540 mg/tablet at an average.

Comparative Example 11

Lactitol Alone

Coating liquid containing 65.00% lactitol and 35.00% water by weight was prepared without use of oxidized acetylated tapioca starch used in Example 16 but using only lactitol.

Coating was performed as in Example 1 with prepared coating liquid to obtain comparative product 11 having a weight of 540 mg/tablet at an average.

Comparative Example 12

Mannitol Alone

Coating liquid containing 30.00% mannitol and 70.00% water by weight was prepared without use of oxidized acetylated tapioca starch and suspension base used in Example 17 but using only mannitol.

Coating was performed as in Example 1 with prepared coating liquid but no coating layer was formed. As a result, comparative product 12 was not obtained.

Comparative Example 13

Sucrose/Gum Arabic

Coating liquid containing 65.00% sucrose, 3.00% gum arabic and 32.00% water by weight was prepared in the same way as in Example 18 except for use of gum arabic instead of oxidized tapioca starch used in Example 18.

Coating was performed as in Example 1 with prepared coating liquid to obtain comparative product 13 having a weight of 540 mg/tablet at an average.

Comparative Tests

Coating layers and coating preparations were assessed, carrying out the following comparative tests about inventive products 1 to 18 used the coating layer according to the present invention and comparative products 1 to 13 produced as comparative examples. Measured items are shown in Tables 4 to 12 respectively classified with each sugar/sugar alcohol.

Comparative Test 1

Measurement of Unbreakable Strength of Coating Layer

Inventive products obtained in the respective Examples and comparative products obtained in the respective comparative examples were repeatedly subjected to free fall from 30 cm above down to marble to count how many times to fall to break the coating layer on the surface.

10 samples were taken respectively from inventive and comparative products two weeks old after production to measure an average value.

In measurement results, inventive products of the present invention proved to be better in unbreakable strength of coating layer than comparative products without oxidized starch and/or acid treated starch.

Comparative Test 2

Percentage of Coating Liquid Wasted in Forming a Coating layer

Loss of coating liquid in forming a coating layer was measured from weight of solid ingredients in coating liquid used to form coating layers over coating centers having a weight of 320 mg/tablet at an average till obtaining coating preparation having an average weight of 540 mg/tablet in production of inventive products obtained in the respective Examples and comparative products obtained in the respective comparative examples.

Loss percentage was obtained by [(weight of solid ingredients of used coating layer)−(weight of solid ingredients of coating layer adhered to coating centers)]÷(weight of solid ingredients of used coating liquid) ×100.

The measurement results confirmed that the present inventive products lose coating liquid in forming a coating layer less than the comparative products lose.

Comparative Test 3

Time Needed for Coating

Time needed for coating layers to be formed over coating centers having an average weight of 320 mg/tablet till obtaining coating preparation having an average weight of 540 mg/tablet was measured in production of inventive products obtained in the respective Examples and comparative products obtained in the respective comparative examples.

The measurement results confirmed that the present inventive products shorten time needed for coating.

Comparative Test 4

Measurement of Time Needed for a Coating Layer to Collapse

The inventive products obtained in the respective Examples and comparative products obtained in the respective comparative examples were tested in accordance with the Pharmacopoeia of Japan by a collapse tester (named NT-2H produced by Toyama Industrial Co., Ltd.) at a temperature of 37° C., amplitude of 55 mm with rise and fall 30 times per minute.

The measurement results confirmed that realization products of the present invention make no significant difference in collapsing time with any sugar/sugar alcohol and can be sufficiently used in place of gum arabic now commonly used as binder for a coating layer.

Comparative Test 5

Measurement of Smoothness of Coating Layer roughness of the surface of coating layer was assessed by scores as marked up with the eyes of 10 trained panelists about the inventive products obtained in the respective Examples and comparative products obtained in the respective comparative examples, based on the following criteria, in order to judge smoothness of the coating layer.

The points system consists in getting 3 in the case of "no rough at all"; 2 in the case of "almost no rough": 1 in the case of "a little rough; and 0 in the case of "rough" and the points are gathered to judge 30 to 26 points to be "smooth" indicated by ◎, 25 to 16 to be "a little smooth" indicated by ◯, 15 to 6 to be "a little rough" indicated by Δ and 5 or less to be "rough" indicated by X.

The measurement results confirmed that realization products of the present invention are excellent in smoothness of the coating layer surface with any sugar/sugar alcohol and are good-looking coating preparation in appearance.

Comparative Test 6

Assessment of Crunchiness of Coating Layer

The respective coating preparations was assessed in crunchiness by scores as marked up by 10 trained panelists, based on their feelings when crunching them in mouth about the inventive products obtained in the respective Examples and comparative products obtained in the respective comparative examples, based on the following criteria, in order to judge crunchiness of the coating layer.

The points system consists in getting 3 in the case of "strongly crunchy"; 2 in the case of "crunchy": 1 in the case of "barely crunchy; and 0 in the case of "not crunchy" and the points are gathered to judge 30 to 26 points to be "very crunchy" indicated by ◎, 25 to 16 to be "a little crunchy" indicated by ◯, 15 to 6 to be "a little poor in crunchiness" indicated by Δ and 5 or less to be "poor in crunchiness" indicated by x.

The measurement results confirmed that realization products of the present invention are excellent in crunchiness with any sugar/sugar alcohol.

Comparative Test 7

Electronic Microscopic Picture of Coating Layer Surface

Coating layers formed on the surface of coating center of inventive product 1 obtained in Example 1 and of comparative product 1 obtained in comparative example 1 were carefully taken away to observe the appearance of the surface at magnification of ×1000 with an electronic microscope (S-2600N produced by Hitachi, Ltd.).

Figure 2:
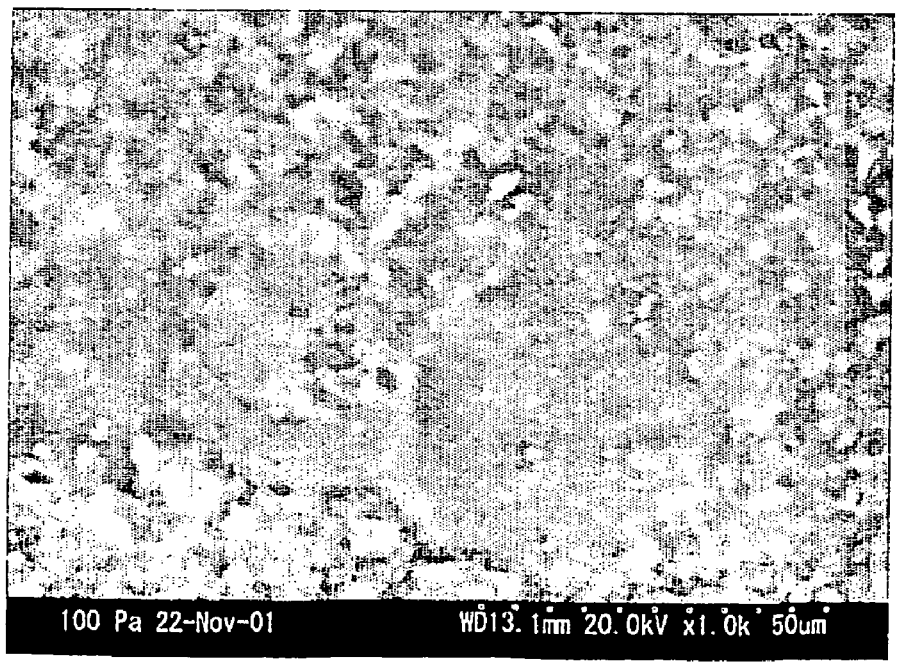
FIG. 2 is an electronic microscopic picture of the coating layer surface of comparative sample 1 with magnification of ×1000.

FIGS. 1 and 2 show electronic microscopic pictures of inventive product 1 and comparative product 1 respectively.

The electronic microscopic pictures confirm that inventive product 1 has a much smoother surface of coating layer than comparative product 1.

TABLE 1

Composition of coating liquid (% by weight)

|  |  | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|---|
|  | Maltitol | 65.00 | 65.00 | 65.00 | 51.00 | 65.00 | 65.00 | 65.00 | 65.00 | 65.00 | 65.00 | 65.00 |
|  | Oxidized acetylated tapioca starch | 3.00 | — | — | 3.00 | — | — | — | — | — | — | — |
|  | Oxidized tapioca starch | — | 3.00 | — | — | — | — | 0.90 | 3.00 | 3.00 | 3.00 | 3.00 |
|  | Oxidized corn starch | — | — | 3.00 | — | — | — | — | — | — | — | — |
|  | Oxidized potato starch | — | — | — | — | 3.00 | — | 2.10 | — | — | — | — |
|  | Oxidized waxy corn starch | — | — | — | — | — | 3.00 | — | — | — | — | — |
| Suspension base | Calcium carbonate | — | — | — | 7.00 | — | — | — | — | — | — | — |
|  | Talc | — | — | — | 7.00 | — | — | — | — | — | — | — |
|  | Water | 32.00 | 32.00 | 32.00 | 32.00 | 32.00 | 32.00 | 32.00 | 32.00 | 32.00 | 32.00 | 32.00 |
|  | Total | 100 | 100 | 100 | 100 | 100 | 100 | 100 | 100 | 100 | 100 | 100 |

TABLE 2

Composition of coating liquid (% by weight)

|  |  | Example 12 | Example 13 | Example 14 | Example 15 | Example 16 | Example 17 | Example 18 |
|---|---|---|---|---|---|---|---|---|
|  | Erythritol | 52.00 | — | — | — | — | — | — |
|  | PALATINIT | — | 52.00 | — | — | — | — | — |
|  | Treharose | — | — | 55.00 | — | — | — | — |
|  | Xylitol | — | — | — | 67.00 | — | — | — |
|  | Lactitol | — | — | — | — | 65.00 | — | — |
|  | Mannitol | — | — | — | — | — | 30.00 | — |
|  | Sucrose | — | — | — | — | — | — | 65.00 |
|  | Oxidized acetylated tapioca starch | — | 5.00 | 5.00 | 3.00 | 3.00 | 5.00 | — |
|  | Acid treated tapioca starch | 5.00 | — | — | — | — | — | — |
|  | Oxidized tapioca starch | — | — | — | — | — | — | 3.00 |
| Suspension base | Calcium carbone | — | — | — | — | — | 10.0 | — |
|  | Talc | — | — | — | — | — | 10.0 | — |
|  | Water | 43.00 | 43.00 | 40.00 | 30.00 | 32.00 | 45.00 | 32.00 |
|  | Total | 100 | 100 | 100 | 100 | 100 | 100 | 100 |

TABLE 3

Composition of coating liquid (% by weight)

|  |  | Comperative Example 1 | Comperative Example 2 | Comperative Example 3 | Comperative Example 4 | Comperative Example 5 | Comperative Example 6 | Comperative Example 7 | Comperative Example 8 | Comperative Example 9 | Comperative Example 10 | Comperative Example 11 | Comperative Example 12 | Comperative Example 13 |
|---|---|---|---|---|---|---|---|---|---|---|---|---|---|---|
|  | Maltitol | 65.00 | 65.00 | 65.00 | 65.00 | 54.00 | 68.00 | — | — | — | — | — | — | — |
|  | Erythritol | — | — | — | — | — | — | 52.00 | — | — | — | — | — | — |
|  | PALATINIT | — | — | — | — | — | — | — | 52.00 | — | — | — | — | — |
|  | Treharose | — | — | — | — | — | — | — | — | 55.00 | — | — | — | — |
|  | Xylitol | — | — | — | — | — | — | — | — | — | 67.00 | — | — | — |
|  | Lactitol | — | — | — | — | — | — | — | — | — | — | 65.00 | — | — |
|  | Mannitol | — | — | — | — | — | — | — | — | — | — | — | 30.00 | — |
|  | Sucrose | — | — | — | — | — | — | — | — | — | — | — | — | 65.00 |
|  | Gum arabic | 3.00 | — | — | — | — | 5.00 | — | — | — | — | — | — | 3.00 |
|  | Tapioca starch | — | 3.00 | — | — | — | — | — | — | — | — | — | — | — |
|  | Tapioca roasted dextrin | — | — | 3.00 | — | — | — | — | — | — | — | — | — | — |
|  | Pullulan | — | — | — | 3.00 | — | — | — | — | — | — | — | — | — |
| Suspension base | Calcium carbonate | — | — | — | — | 7.00 | — | — | — | — | — | — | — | — |

TABLE 3-continued

| | Comperative Example 1 | Comperative Example 2 | Comperative Example 3 | Comperative Example 4 | Comperative Example 5 | Comperative Example 6 | Comperative Example 7 | Comperative Example 8 | Comperative Example 9 | Comperative Example 10 | Comperative Example 11 | Comperative Example 12 | Comperative Example 13 |
|---|---|---|---|---|---|---|---|---|---|---|---|---|---|
| | Composition of coating liquid (% by weight) | | | | | | | | | | | | |
| Talc | — | — | — | — | 7.00 | — | — | — | — | — | — | — | — |
| Water | 32.00 | 32.00 | 32.00 | 32.00 | 32.00 | 32.00 | 43.00 | 48.00 | 45.00 | 33.00 | 35.00 | 70.00 | 32.00 |
| Total | 100 | 100 | 100 | 100 | 100 | 100 | 100 | 100 | 100 | 100 | 100 | 100 | 100 |

TABLE 4

Results of inventive products 1 to 11 with use of Maltitol

| | Example 1 Inventive Product 1 | Example 2 Inventive Product 2 | Example 3 Inventive Product 3 | Example 4 Inventive Product 4 | Example 5 Inventive Product 5 | Example 6 Inventive Product 6 | Example 7 Inventive Product 7 | Example 8 Inventive Product 8 | Example 9 Inventive Product 9 | Example 10 Inventive Product 10 | Example 11 Inventive Product 11 |
|---|---|---|---|---|---|---|---|---|---|---|---|
| Unbreakable strength | 11.2 | 10.2 | 11.0 | 10.0 | 10.1 | 11.0 | 10.5 | 8.0 | 12.0 | 10.2 | 10.0 |
| Waste(%) | 3.1 | 4.2 | 4.2 | 4.3 | 3.5 | 3.3 | 3.2 | 3.5 | 3.0 | 3.2 | 3.0 |
| Time needed for coating | 16 hrs 42 min | 16 hrs 42 min | 16 hrs 58 min | 16 hrs 42 min | 16 hrs 50 min | 16 hrs 40 min | 16 hrs 45 min | 11 hrs 50 min | 11 hrs 20 min | 9 hrs 50 min | 9 hrs 10 min |
| Time needed for collapse | 15 min 23 sec | 15 min 19 sec | 15 min 20 sec | 15 min 08 sec | 15 min 20 sec | 15 min 22 sec | 15 min 21 sec | 15 min 20 sec | 15 min 22 sec | 15 min 40 sec | 16 min 10 sec |
| Smoothness | ◎ | ◎ | ◎ | ◎ | ◎ | ◎ | ◎ | ○ | ◎ | ○ | ○ |
| Crunchiness | ◎ | ◎ | ◎ | ◎ | ◎ | ◎ | ◎ | ○ | ◎ | ○ | ○ |

TABLE 5

Results of comparative products 1 to 6 with use of Maltitol

| | Comperative Example 1 Comperative Product 1 | Comperative Example 2 Sugar coating layer non-formable | Comperative Example 3 Comperative Product 3 | Comperative Example 4 Comperative Product 4 | Comperative Example 5 Comperative Product 5 | Comperative Example 6 Comperative Product 6 |
|---|---|---|---|---|---|---|
| Unbreakable strength | 4.3 | — | 7.7 | 7.5 | 3.4 | 3.9 |
| Waste(%) | 9.7 | — | 8.0 | 8.9 | 13.5 | 11.0 |
| Time needed for coating | 18 hrs 32 min | — | 17 hrs 56 min | 18 hrs 00 min | 19 hrs 05 min | 19 hrs 52 min |
| Time needed for collapse | 15 min 08 sec | — | 14 min 29 sec | 15 min 15 sec | 14 min 03 sec | 14 min 19 sec |
| Smoothness | ◎ | — | ○ | X | Δ | ◎ |
| Crunchiness | ◎ | — | Δ | Δ | Δ | ○ |

TABLE 6

Results with use of Erythritol

| | Example 12 Inventive Product 12 | Comparative Example 7 Comparative Product 7 |
|---|---|---|
| Unbreakable strength | 4.9 | 1.5 |
| Waste(%) | 7.9 | 15.6 |
| Time needed for coating | 18 hrs 32 min | 19 hrs 42 min |
| Time needed for collapse | 14 min 08 sec | 14 min 05 sec |
| Smoothness | ◎ | Δ |
| Crunchiness | ○ | x |

TABLE 7

Results with use of PALATINIT

| | Example 13 Inventive Product 13 | Comparative Example 8 Comparative Product 8 |
|---|---|---|
| Unbreakable strength | 5.0 | 1.4 |
| Waste(%) | 6.6 | 17.6 |
| Time needed for coating | 18 hrs 22 min | 20 hrs 12 min |
| Time needed for collapse | 14 min 23 sec | 14 min 15 sec |
| Smoothness | ◎ | Δ |
| Crunchiness | ○ | x |

TABLE 8

Results with use of Treharose

|  | Example 14 Inventive Product 14 | Comparative Example 9 Comparative Product 9 |
|---|---|---|
| Unbreakable strength | 4.8 | 1.3 |
| Waste(%) | 6.5 | 16.0 |
| Time needed for coating | 18 hrs 10 min | 20 hrs 04 min |
| Time needed for collapse | 14 min 05 sec | 14 min 00 sec |
| Smoothness | ○ | Δ |
| Crunchiness | ○ | Δ |

TABLE 9

Results with use of Xylitol

|  | Example 15 Inventive Product 15 | Comparative Example 10 Comparative Product 10 |
|---|---|---|
| Unbreakable strength | 6.8 | 2.4 |
| Waste(%) | 4.8 | 12.2 |
| Time needed for coating | 16 hrs 50 min | 19 hrs 52 min |
| Time needed for collapse | 14 min 30 sec | 14 min 05 sec |
| Smoothness | ⊙ | ⊙ |
| Crunchiness | ○ | Δ |

TABLE 10

Results with use of Lactitol

|  | Example 16 Inventive Product 16 | Comparative Example 11 Comparative Product 11 |
|---|---|---|
| Unbreakable strength | 6.9 | 2.6 |
| Waste(%) | 5.0 | 11.8 |
| Time needed for coating | 17 hrs 00 min | 20 hrs 05 min |
| Time needed for collapse | 15 min 18 sec | 14 hrs 10 sec |
| Smoothness | ⊙ | ○ |
| Crunchiness | ○ | Δ |

TABLE 11

Results with use of Mannitol

|  | Example 17 Inventive Product 17 | Comparative Example 12 Sugar coating layer non-formable |
|---|---|---|
| Unbreakable strength | 4.5 | — |
| Waste(%) | 8.1 | — |
| Time needed for coating | 18 hrs 50 min | — |
| Time needed for collapse | 14 min 20 sec | — |
| Smoothness | ○ | — |
| Crunchiness | Δ | — |

TABLE 12

Results with use of Sucrose

|  | Example 18 Inventive Product 18 | Comparative Example 13 Comparative Product 13 |
|---|---|---|
| Unbreakable strength | 8.0 | 3.2 |
| Waste(%) | 2.8 | 9.5 |
| Time needed for coating | 14 hrs 35 min | 16 hrs 10 min |
| Time needed for collapse | 15 min 18 sec | 15 min 10 sec |
| Smoothness | ⊙ | ○ |
| Crunchiness | ○ | Δ |

The invention claimed is:

1. A hard coating preparation for food or medecine having a hard coating layer comprising (a) any one sugar/sugar alcohol selected from the group consisting of maltitol, xylitol, erythritol, mannitol, lactitol, trehalose, sucrose, and a mixture of α-D-glucopyranosyl-1,6-sorbitol and α-D-glucopyranosyl-1,1-mannitol, and (b) oxidized starch.

2. The hard coating preparation according to claim 1, wherein the coating layer comprises, as solid content, 35.00 to 99.99% sugar/sugar alcohol and 0.01 to 65.00% oxidized starch by weight as calculated on a solid basis.

3. The hard coating preparation according to claim 1 or 2, further comprising a coating reinforcing agent and/or suspension base.

4. The hard coating preparation according to claim 1 to 2, wherein the sugar alcohol is maltitol.

5. A coating liquid for food or medecine comprising, in the form of dissolved solid ingredients, 80.00 to 99.99% of a sugar/sugar alcohol by weight and 0.01 to 20.00% of an oxidized starch by weight, calculated on a solid basis, wherein the sugar/sugar alcohol is selected from the group consisting of maltitol, xylitol, erythritol, mannitol, lactitol, trehalose, sucrose and a mixture of α-D-glucopyranosyl-1,6-sorbitol and α-D-glucopyranosyl-1,1-mannitol.

6. The coating liquid according to claim 5, further comprising a coating reinforcing agent and/or suspension base.

7. The coating liquid according to claim 5 or 6, wherein the sugar alcohol is maltitol.

8. A process of manufacturing a hard coating preparation comprising alternately repeating a liquid pouring step where the coating liquid according to claim 5 or 6 is poured on a coating center and a drying step where the coating center wet with the liquid is dried.

9. The process of manufacturing a hard coating preparation according to claim 8, further comprising a powder dusting step to dust the coating center with a mixture powder wherein the mixture powder is any one or two or more powder(s) selected from the group consisting of maltitol, xylitol, erythritol, mannitol, lactitol, trehalose, sucrose, a mixture of α-D-glucopyranosyl-1,6-sorbitol and α-D-glucopyranosyl-1,1-mannitol, oxidized starch, acid treated starch, suspension base, and coating reinforcing agent.

10. The process of manufacturing a hard coating preparation according to claim 8, wherein said coating liquid further mixed and suspended with a powder consisting of any one or two or more of the solid ingredients contained in the coating liquid.

* * * * *